(12) United States Patent
Choi et al.

(10) Patent No.: US 8,784,854 B2
(45) Date of Patent: Jul. 22, 2014

(54) COSMETIC PRODUCT COMPRISING UV-BLOCKING COSMETIC COMPOSITION IMPREGNATED INTO EXPANDED URETHANE FOAM

(71) Applicant: Amorepacific Corporation, Seoul (KR)

(72) Inventors: Kyung Ho Choi, Suwon-si (KR); Min Kyung Shim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 13/632,343

(22) Filed: Oct. 1, 2012

(65) Prior Publication Data

US 2013/0045259 A1 Feb. 21, 2013

Related U.S. Application Data

(63) Continuation-in-part of application No. 12/933,498, filed as application No. PCT/KR2009/001407 on Mar. 19, 2009, now abandoned.

(30) Foreign Application Priority Data

Mar. 20, 2008 (KR) .............. 2008-0025947

(51) Int. Cl.
| | |
|---|---|
| *A61K 8/06* | (2006.01) |
| *A61Q 1/02* | (2006.01) |
| *A61Q 17/04* | (2006.01) |
| *A61Q 1/08* | (2006.01) |
| *A61Q 1/04* | (2006.01) |
| *A61Q 1/10* | (2006.01) |
| *A61K 8/02* | (2006.01) |
| *A61K 8/87* | (2006.01) |

(52) U.S. Cl.
CPC ............ *A61K 8/87* (2013.01); *A61K 2800/244* (2013.01); *A61Q 1/02* (2013.01); *A61Q 17/04* (2013.01); *A61K 2800/87* (2013.01); *A61Q 1/08* (2013.01); *A61Q 1/04* (2013.01); *A61K 8/06* (2013.01); *A61Q 1/10* (2013.01); *A61K 8/0216* (2013.01)
USPC ........................... 424/401; 424/59

(58) Field of Classification Search
CPC .................. A61Q 1/02; A61K 8/87
USPC ........................... 424/401, 59
See application file for complete search history.

(56) References Cited

U.S. PATENT DOCUMENTS

| | | | |
|---|---|---|---|
| 6,060,041 A | 5/2000 | Candau et al. | |
| 6,391,233 B1 * | 5/2002 | Otani et al. | 264/49 |
| 2003/0216483 A1 | 11/2003 | Hermann et al. | |

FOREIGN PATENT DOCUMENTS

| | | |
|---|---|---|
| CN | 1658910 A | 8/2005 |
| JP | 57-024305 | 2/1982 |
| JP | 2003-12457 A | 1/2003 |
| JP | 2007-330771 A | 12/2007 |
| KR | 2006-0025166 | 3/2006 |
| KR | 2006-0040151 A | 5/2006 |
| WO | WO 01/16200 | 3/2001 |
| WO | WO 03/011937 | 2/2003 |

OTHER PUBLICATIONS

JP 2003-012457_machine_translation (2003).*
International Search Report for PCT/KR2009/001407, mailed Oct. 26, 2009.
Notice of Preliminary Rejection in Korean Appln. SN 10-2008-0025947 dated Oct. 11, 2011.
First Notification of Office Action (with English translation in CN 200980109690.1 dated Aug. 5, 2011.
Brief explanation of references.

* cited by examiner

*Primary Examiner* — Jake Vu
(74) *Attorney, Agent, or Firm* — Nixon & Vanderhye, P.C.

(57) ABSTRACT

The present invention relates to a cosmetic product comprising a UV-blocking W/O or O/W composition of low viscosity packaged in a compact-type container. More specifically, the invention relates to a UV-blocking cosmetic product prepared by impregnating a UV-blocking W/O or O/W cosmetic composition of low viscosity into expanded urethane foam, preparing a compact formulation from the expanded urethane foam impregnated with the composition, and then packaging the compact formulation in a cosmetic container. Thus, the UV-blocking cosmetic product is convenient for the user to carry and use and also has a skin-cooling effect.

7 Claims, 5 Drawing Sheets

COSMETIC PRODUCT COMPRISING UV-BLOCKING COSMETIC COMPOSITION IMPREGNATED INTO EXPANDED URETHANE FOAM

This application is a continuation-in-part of U.S. application Ser. No. 12/933,498 filed Sep. 20, 2010, which in turn is the U.S. national phase of International Application No. PCT/KR2009/001407 filed 19 Mar. 2009, which designated the U.S. and claims priority to KR Application No. 10-2008-0025947 filed 20 Mar. 2008, the entire contents of each of which are hereby incorporated by reference.

TECHNICAL FIELD

The present invention relates to a UV-blocking product that is prepared by impregnating a UV-blocking W/O (water-in-oil) or O/W (oil-in-water) emulsion cosmetic composition of low-viscosity into expanded urethane foam, and thus allows the active ingredient of the composition to be efficiently applied to the skin and is convenient to use and carry.

BACKGROUND ART

Exposure to UV rays from sunlight is a major cause of skin erythema, edema, freckles or skin cancer. Recently, many studies on various skin diseases caused by UV rays have been actively conducted.

Generally, UV rays are classified according to wavelength into UV-C (240-280 nm), UV-B (280-320 nm) and UV-A (320-400 nm). UV-C radiation does not reach the Earth's surface because it is absorbed by the ozone layer, but UV-B penetrates the epidermis so that it causes erythema, freckles, edema, etc. It is known that UV-A penetrates into the dermal layer of the skin to cause skin aging and skin irritation, thereby stimulating skin cancer, wrinkles and melamine formation.

Public interest in products for protecting the skin from the sun has significantly increased and, as a result, UV blocking products having various sun protection factors (SPFs) have appeared in the market. UV blocking products are generally prepared in the form of cream or lotion and can be classified, according to the composition of the inner phase and outer phase of emulsion, into W/O type (water-in-oil) and O/W type (oil-in-water).

UV blocking products have been used mainly in the summer season. However, recently, as life styles have changed due to an increase in the number of peoples enjoying leisure and as the recognition of the harmfulness of UV radiation has increased, the demand for the use of UV blocking products in all four seasons, rather than only in summer, has increased. Accordingly, the consumer demand has increased for UV blocking products having increased usability and convenience to use.

In the prior art, UV-blocking W/O or O/W emulsion products have been used in the state in which they are contained in tube or pump containers in order to set the viscosity and to improve the usability. However, these products are relatively inconvenient to carry and use, thus causing inconvenience in make-up correction. Particularly in summer, cosmetic products that lower the skin temperature to give a cold feel are more preferred. However, because the compositions are applied to the skin by hand, cosmetic products comprising cosmetic compositions in tube or pump containers cannot give a cold feel due to the heat of hand used to apply them. In addition, after the use of the cosmetic compositions, the hand should be washed to remove the contamination and stickiness caused thereon by applying the cosmetic compositions.

DISCLOSURE OF INVENTION

The present inventors have prepared a compact formulation by impregnating a UV-blocking W/O or O/W composition of low viscosity into expanded urethane foam, thereby completing a cosmetic product which ensures product stability, is convenient to use and carry, maintains the UV-blocking effect for a long time, eliminates the need to wash an hand, and has a skin-cooling effect.

An object of the present invention is therefore to provide a UV-blocking product that has a good UV-blocking effect and, at the same time, is convenient to use and carry.

The present invention provides a UV-blocking cosmetic compact product containing an expanded urethane foam impregnated with a UV-blocking water-in-oil (W/O) or oil-in-water (O/W) emulsion composition of low-viscosity containing an oil-phase component, an emulsifying agent, an organic or inorganic UV-blocking agent, a pigment and a water-phase component.

The oil-phase component that is mainly used in the present invention is at least one selected from among: vegetable oils, including rose hip oil, safflower oil, peach seed oil, meadowfoam seed oil and sunflower seed oil; synthetic esters or hydrocarbons, including dicaprylyl carbonate, squalane, neopentyl glycol diheptanoate, tocopheryl acetate, trioctanoin, C12-15 alkyl benzoate, C12-15 alkyl ethylhexanoate, octyldodecyl myristate, tricaprylin, octyldodecyl stearoyl stearate, bis-hydroxyethoxypropyl dimethicone, caprylic/capric triglyceride, isotridecyl isononanoate, polyglyceryl-2 triisostearate, diisostearyl malate, dipentaerythrite fatty acid ester, cetyl octanoate and ozokerite, silicone oils, including phenyl trimethicone, cyclomethicone, dimethicone and decamethylcyclopentasiloxane; fatty alcohols, fatty acids, and higher alcohols.

When the oil-phase component forms the outer phase of the composition, that is, when it is used in a water-in-oil (W/O) composition, it is contained in an amount of 20-80 wt % based on the total weight of the composition, and when the oil-phase component forms the inner phase of the composition, that is, when it is used in an oil-in-water (O/W) composition, it is contained in an amount of 30-70 wt % based on the total weight of the composition. If the content of the oil-phase component in the W/O emulsion composition is less than 20 wt %, the composition will have poor stability or excessively high viscosity, and thus it will impart a heavy feel to the skin and be sticky, thus deteriorating the usability of the composition. If the content of the oil-phase component in the W/O emulsion composition is greater than 80 wt %, the composition will have poor stability. On the other hand, if the content of the oil-phase component in the O/W emulsion composition is less than 30 wt %, the stability of the composition will be reduced due to excessively low viscosity, and if the content is greater than 70 wt %, the viscosity of the composition will be excessively increased.

The emulsifying agent that is used in the present invention is preferably a nonionic surfactant having an HLB ranging from 1 to 17. Particularly, in a W/O emulsion, a nonionic surfactant having a low HLB ranging from 1 to 6 is preferably used, and in an O/W emulsion, a nonionic surfactant having a low HLB ranging from 1 to 6 is preferably used in combination with a nonionic surfactant having a high HLB ranging from 8 to 17.

Specifically, the emulsifying agent that is used in the present invention may be at least one selected from among cyclopentasiloxane, PEG/PPG-18/18 dimethicone, glycol stearate, sorbitan sesquioleate, glyceryl oleate, glycol distearate, propylene glycol monostearate, glyceryl stearate, sorbitan stearate, PEG-30 dipolyhydroxystearate, PEG-10 dimethicone, cyclopentasiloxane/PEG.PPG-19.19 dimethicone, sorbitan isostearate, lauryl PEG.PPG-18.18 methicone, cetyl PEG.PPG-10.1 dimethicone, lauryl PEG-9 polydimethylsiloxyethyl dimethicone, PPG-26-Buteth-26, PEG-40 hydrogenated castor oil, PEG-30 hydrogenated castor oil, ceteareth-12, PEG-60 glyceryl isostearate, PEG-100 stearate, polysorbate 20, polysorbate 80, polyglyceryl-10 pentastearate, behenyl alcohol, sodium stearoyl lactylate, methoxy PEG-114/polyepsilon caprolactone, potassium cetyl phosphate, polysorbate 60, polyglyceryl-10 stearate, inulin lauryl carbamate, cetearyl olivate/sorbitan olivate, PEG-60 hydrogenated castor oil, polyglyceryl-3 methylglucose distearate, PEG-5 rapeseed sterol, sucrose polystearate/hydrogenated polyisobutene, C14-22 alcohols, C12-20 alkyl glucosides, cetearyl alcohol/cetearyl glucoside, hydrogenated lecithin, arachidyl alcohol, behenyl alcohol, arachidyl glucoside, olive oil PEG-8 esters, sucrose fatty acid ester, etc.

Also, the emulsifying agent is contained in an amount of 0.01-10 wt % based on the total weight of the composition. If the content of the emulsifying agent in the composition is less than 0.01 wt %, an emulsion will not be formed or the stability of the composition will be poor, and if the content of the emulsifying agent is more than 10 wt %, the composition will be sticky and can give out an offensive odor due to the emulsifying agent.

The UV-blocking agent that is used in the present invention may be selected from among organic UV-blocking agents and inorganic UV-blocking agents, which can be used alone or in a mixture of two or more thereof. Specifically, examples of organic UV-blocking agents that can be used in the present invention include octyl methoxycinnamate, octyl salicylate, octocrylene, butyl methoxydibenzoylmethane, oxybenzone, octyltriazone, menthyl anthranilate, 3,4-methylbenzylidene camphor, isoamyl-P-methoxycinnamate, bis-ethylhexylphenol methoxyphenyl triazine, methylene bis-benzotrizolyl tetramethylbutylphenol, etc. Examples of inorganic UV-blocking agents that can be used in the present invention include titanium dioxide having a mean particle size of 5-100 nm, zinc oxide having a mean particle size of 5-300 nm, iron oxide having a mean particle size of 5-300 nm, etc. Herein, as the mean particle size of inorganic UV-blocking agents increases, the whitening of the composition will become more severe upon application to the skin, and thus the commercial value of the composition will be reduced. However, if the particle size of inorganic UV-blocking agents is too small, they can penetrate into the skin to cause skin irritation. Accordingly, the mean particle size of inorganic UV-blocking agents is preferably less than 300 nm in view of the whitening phenomenon, and is preferably 10-50 nm in view of whitening together with skin irritation.

The UV-blocking agent is contained in an amount of 1-35 wt % based on the total weight of the composition. If the content of the UV-blocking agent is less than 1 wt %, SPF(sun protection factor) is less than 10 and thereby results in insignificant UV-blocking effect, and if the content of the UV-blocking agent is greater than 35 wt %, the whitening and glossiness of the composition will become severe or the composition can cause skin irritation.

The pigment that is used in the present invention is a component excluding the inorganic UV-blocking agent and may be at least one selected from among PMMA (polymethylmethacrylate), silica, nylon, polyurethane, ultramarine, iron oxide, pearl, synthetic mica, mica, talc, sericite and boron nitrate. The pigment is contained in an amount of 0.1-20 wt % based on the total weight of the composition. If the content of the pigment in the composition is less than 0.1 wt %, its effects such as skin adhesion, color expression and thickening power will be insignificant, whereas if the pigment content is less than or equal to 20 wt %, it will show effects such as skin adhesion, color expression and thickening power, but if the pigment content is more than 20 wt %, it will excessively increase the viscosity of the composition, thus imparting a hard feel to the skin and reducing the stability of the emulsion.

The water-phase component that is used in the present invention may be at least one selected from the group consisting of purified water, propylene glycol, 1,3-butylene glycol, glycerin, 1,3-PG (propylene glycol), sorbitol, xylitol, hexylene glycol, pentylene glycol, caprylyl glycol, PEG (polyethylene glycol), and various polysaccharides.

The water-phase component, when used in a W/O emulsion composition, is contained in an amount of 30-70 wt % based on the total weight of the composition. Further, if the water-phase component, when used in an O/W emulsion composition, is contained in an amount of 20-80 wt % based on the total weight of the composition. If the content of the water-phase component in the W/O emulsion composition is less than 30 wt %, the viscosity of the composition will be excessively low so that the stability of the composition will be reduced, and if the content of the water-phase component is greater than 70 wt %, the viscosity of the composition will be excessively increased. Also, if the content of the water-phase component in the O/W emulsion composition is less than 20 wt %, the viscosity of the composition will be excessively increased, thus reducing the usability of the composition, and if the content is more than 80 wt %, the viscosity of the composition will be excessively reduced, thus reducing the stability of the composition.

In addition to the above-described components, at least one selected from among preservatives, fragrances and other additives may additionally be added to the UV-blocking composition. Among materials that can be used as preservatives, parabens such as methyl paraben, propyl paraben, butyl paraben or ethyl paraben may be added to the oil phase of the composition, and substances such as phenoxy ethanol may be added to the water phase. Also, fragrance is added to the oil phase of the W/O or O/W emulsion composition in the final step of the process of preparing the composition.

The UV-blocking W/O or O/W emulsion composition of the present invention has a low viscosity of 5000-15000 cps. If the viscosity of the W/O or O/W emulsion composition is less than 5000 cps, the separation between the oil phase and the water phase will occur immediately after the preparation of the emulsion, thus making it difficult to uniformly impregnate an emulsion composition into expanded urethane foam, and if the viscosity is greater than 15000 cps, the composition will be sticky upon application to the skin and will impart a heavy feel to the skin, and thus the commercial value of the composition will be reduced.

Figure 1:
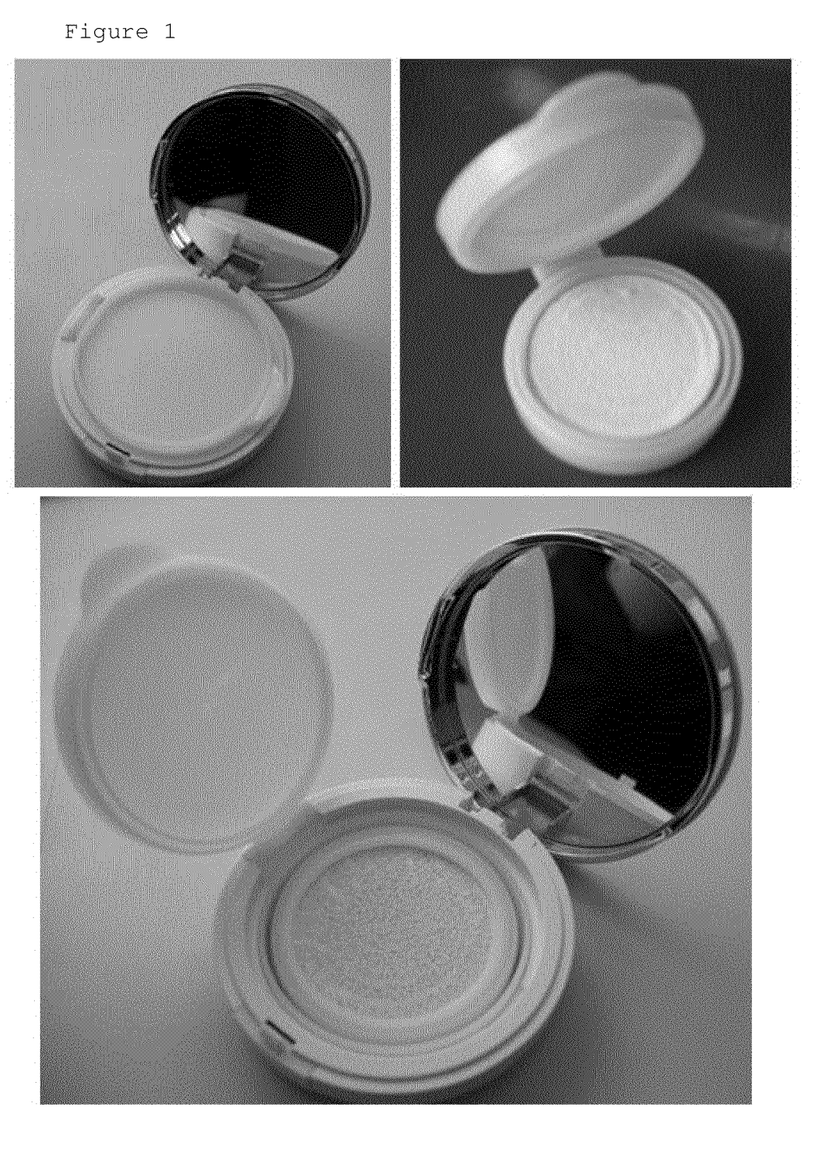
FIG. 1 is a set of photographs showing a cosmetic container containing a compact cosmetic product including expanded urethane foam.

The UV-blocking composition of the present invention is impregnated into expanded urethane foam to prepare a compact formulation which is then packaged in a cosmetic container. The compact-type container is easier to use and carry than a tube- or pump-type container, but a flowable cosmetic composition tends to overflow the container or to be contaminated, and thus the flowability of the flowable cosmetic composition should be abruptly reduced. For this reason, the compact-type container includes expanded urethane foam. FIG. 1 shows a cosmetic container which can contain a compact cosmetic product including expanded urethane foam.

With respect to expanded urethane foam that is impregnated with the UV-blocking composition of the present invention, closed cell urethane foam cannot be impregnated with the UV-blocking composition, because pores are closed within urethane. For this reason, open cell urethane foam is preferably used.

Also, the expanded urethane foam that is used in the present invention should have suitable hardness. Preferably, open cell urethane foam having a hardness of 10-70 as measured before impregnation with a durometer hardness tester (type F; manufactured by ASKER) may be used. If the expanded urethane foam is excessively soft, the cosmetic composition impregnated in the expanded urethane foam will excessively flow out when applying make-up by hands or a cosmetic applicator (mainly NBR puff), and if the expanded urethane foam is excessively hard, the cosmetic composition will not easily flow out.

Advantageous Effects

According to the present invention, a UV-blocking W/O or O/W emulsion composition is impregnated into expanded urethane foam, which is then packaged in a compact-type container. Thus, the present invention can provide a UV-blocking cosmetic composition having increased formulation stability, improved portability and convenience and an improved skin-cooling effect.

BEST MODE FOR CARRYING OUT THE INVENTION

Hereinafter, the present invention will be described in further detail by way of examples and test examples with reference to the accompanying drawings. Theses examples and test examples are merely intended to facilitate the understanding of the present invention, and the scope of the present invention is not limited thereto.

REFERENCE EXAMPLES

According to the components and contents shown in Table below, W/O emulsion make-up cosmetic compositions of Reference Examples 1 and 2 were prepared.

For this purpose, a UV-blocking agent was dissolved in oil-phase components and emulsified, and then a surfactant was added thereto. The mixture was heated to 80° C. and uniformly stirred, and then a pigment was added thereto and uniformly stirred. Meanwhile, in a separate mixer, water-phase components were mixed with each other, heated to 80° C. and stirred to form a water phase solution. The water phase solution was added slowly to the oil phase, and the mixture was emulsified using a homomixer. The emulsion was cooled to 50° C., and then skin protection components and fragrance were added thereto. The resulting mixture was cooled, thus obtaining a UV-blocking W/O emulsion composition of low viscosity.

TABLE 1

| | | Ingredients (content: wt %) | Reference Example 1 | Reference Example 2 |
|---|---|---|---|---|
| Oil-phase | Oil-phase component | Ozokerite | 0.1 | 1.0 |
| | | Dicaprylyl Carbonate | 10.00 | 10.00 |
| | Antiseptics | Methyl Paraben | 0.100 | 0.100 |
| | UV-blocking agent | Octyl methoxycinnamate | 7.000 | 7.000 |
| | | Isoamyl p-methoxycinnamate | 2.000 | 2.000 |
| | Pigment | Disteardimonium Hectorite | 0.20 | 1.50 |
| | Oil-phase component | Decamethyl-cyclopentasiloxane | 16.00 | 16.00 |
| | Emulsifying agent | Sorbitan Sesquioleate | 2.000 | 2.000 |
| | | Lauryl PEG. PPG-18.18 methicone | 1.500 | 1.500 |
| | Pigment | Polymethylmethacrylate | 5.00 | 5.00 |
| | | Titanium dioxide/Aluminum Hydroxide/Stearic Acid | 7.00 | 7.00 |
| Water-phase | | Water | To 100 | To 100 |
| | Moisturizer | Glycerin | 8.000 | 8.000 |
| | Emulsion stabilizer | Salt | 1.00 | 1.00 |
| | | Perfume | 0.400 | 0.400 |
| | Total Sum | | 100.000 | 100.000 |

In addition, according to the components and contents shown in Table 2 below, O/W emulsion make-up cosmetic compositions of Reference Examples 3 and 4 were prepared.

For this purpose, in a mixer, oil-phase components were dissolved by heating to 70 and dispersed using a homogenizer, thus preparing an oil-phase component mixture.

In a separate mixer, water-phase components (excluding water-phase thickening agent and fragrance) were dissolved by heating to 70, and the above-prepared oil-phase component mixture was added thereto. The resulting mixture was subjected to oil-in-water emulsification using a homogenizer at 70 for 4-5 minutes. A thickening agent, such as carbomer, and fragrance were added thereto and mixed using a homogenizer for 3 minutes. Then, the emulsion was degassed using a degassing device, thus preparing O/W emulsion make-up cosmetic compositions to be used as samples.

TABLE 2

| | | Ingredients (content: wt %) | Reference Example 3 | Reference Example 4 |
|---|---|---|---|---|
| Oil phase | Oil-phase component | Cetostearyl Alcohol | 0.1 | 0.5 |
| | | Dicaprylyl | 10.00 | 10.00 |

TABLE 2-continued

| | | Ingredients (content: wt %) | Reference Example 3 | Reference Example 4 |
|---|---|---|---|---|
| | | Carbonate | | |
| | Antiseptics | Methyl Paraben | 0.100 | 0.100 |
| | UV-blocking agent | Octyl methoxycinnamate | 7.000 | 7.000 |
| | | Isoamyl p-methoxycinnamate | 2.000 | 2.000 |
| | Oil-phase component | Decamethyl-cyclopentasiloxane | 15.00 | 15.00 |
| | Emulsifying agent | Glyceryl Stearate | 0.7 | 0.7 |
| | Pigment | Polymethylmethacrylate | 1.00 | 1.00 |
| Water phase | | Water | To 100 | To 100 |
| | Moisturizer | Glycerin | 8.000 | 8.000 |
| | Thickener | Carbomer | 0.1 | 0.2 |
| | Emulsifying agent | Glyceryl Stearate/PEG-100 Stearate | 0.5 | 0.5 |
| | Emulsifying agent | Polyglyceryl-3 Methyl Glucose Distearate | 1.5 | 1.5 |
| | Pigment | Titanium dioxide | 3.0 | 3.0 |
| | Dispersant | TES-Sterate solution | 3.0 | 3.0 |
| | | Perfume | 0.400 | 0.400 |
| | | Total sum | 100.000 | 100.000 |

In Tables 1 and 2 above, disteardimonium hectoriteas a pigment phase serving as a thickening agent, the pigment polymethylmethacrylate is a pure extender pigment, and titanium dioxide/aluminum hydroxide/stearic acid is an inorganic UV-blocking agent.

TEST EXAMPLE 1

FORMULATION STABILITY TEST

Formulation stability was tested with the W/O emulsion make-up cosmetic compositions of Reference Examples 1 and 2 and the O/W emulsion make-up cosmetic compositions of Reference Examples 3 and 4. In Examples 1 to 4 corresponding to the compositions of Reference Examples 1 to 4, respectively, the compositions were impregnated into expanded urethane foam having a hardness of 40 as measured after impregnation with an ASKER hardness tester (type F). In Comparative Examples 1 to 4 corresponding to the composition of Reference Examples 1 to 4, respectively, the compositions were stored in plastic containers, Comparative Example 5 was an urethane foam in the form of a thin sheet 48 mm in diameter and 0.2mm thick as impregnated with Reference Example 1, and the stability thereof was tested under the conditions shown in Table 3 below. The test results are shown in Table 3. In addition, the results of storing the compositions of Example 1 and Comparative Example 1 at 50 for 2 hours are shown in FIG. 2.

TABLE 3

| | Passage of 10 days at 45° C. | Cycle [45° C. →30° C. → freeze(–10° C.) every 8 hours] passage of 5 days | Passage of 2 hours at 50° C. |
|---|---|---|---|
| Example 1 | Stable | Stable | Stable in appearance |
| Example 2 | Stable | Stable | Stable in appearance |
| Example 3 | Stable | Stable | Stable in appearance |
| Example 4 | Stable | Stable | Stable in appearance |
| Comparative Example 1 | phase-separated | phase-separated | Bubbles generated in appearance |
| Comparative Example 2 | phase-separated | phase-separated | Bubbles generated in appearance |
| Comparative Example 3 | phase-separated | phase-separated | white bands occurred on the surface |
| Comparative Example 4 | phase-separated | phase-separated | white bands occurred on the surface |
| Comparative Example 5 | Separated | Separated | Separated |

Figure 2:
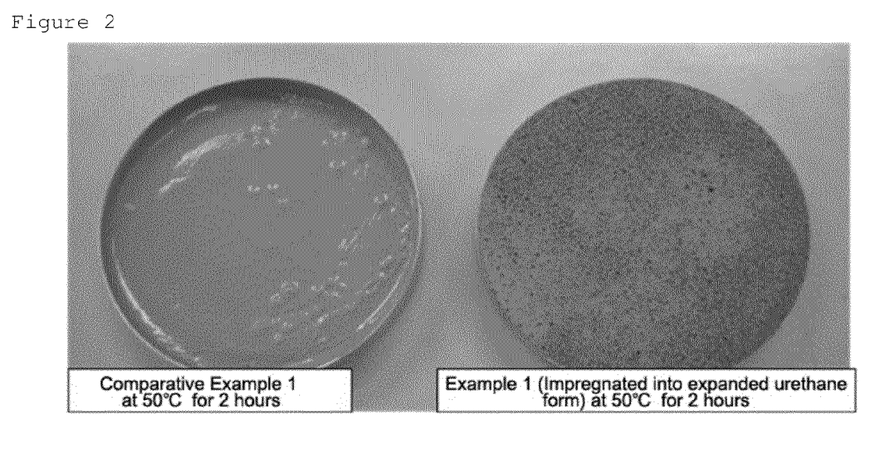
FIG. 2 is a photographs showing the results of storing compositions of Example 1 and Comparative Example 1 at 50° C. for 2 hours.

As can be seen in Table 3 and FIG. 2, in the case of Comparative Examples 1 and 2 in which the W/O emulsion make-up cosmetic compositions of low viscosity according to the present invention were stored in the plastic containers, the formulation was phase-separated with the passage of time or was instable due to generated bubbles, suggesting that the formulation was unstable. Also, in the case of Comparative Examples 3 and 4 in which the O/W emulsion make-up cosmetic compositions were stored in the plastic containers, the formulation was phase-separated with the passage of time, and white bands occurred on the surface of the formulation. Further, the urethane foam in the form of a thin sheet according to Comparative Example 5 underwent separation of formulation immediately after impregnation and thus became unstable. In contrast thereto, in the case of Examples 1 to 4 in which the compositions were impregnated into expanded urethane foam, the formulation was stable even when the temperature changed and the time elapsed.

TEST EXAMPLE 2

TEST for the EFFECT of LOWERING the SKIN TEMPERATURE

In Example 5, the W/O emulsion make-up cosmetic composition of Reference Example 1 was impregnated into expanded urethane foam having a hardness of 40 as measured after impregnation with an ASKER hardness tester (type F), and then the composition was applied to the skin using the cosmetic applicator NBR puff. In Comparative Examples 6 and 7, the composition of Reference Example 1 was placed in a tube container or a pump container, and then applied to the skin by hand. After applying each composition to the skin, a change in the skin temperature was measured, thus determining the effect of lowering the skin temperature.

In Example 6, the O/W emulsion make-up cosmetic composition of Reference Example 3 was impregnated into expanded urethane foam having a hardness of 40 as measured after impregnation with an ASKER hardness tester (type F), and then the composition was applied to the skin using the cosmetic applicator NBR puff. In Comparative Examples 8 and 9, the composition of Reference Example 3 was placed in a tube container or a pump container and then applied to the skin by hand. After applying each composition to the skin, a change in the skin temperature was measured, thus determining the effect of lowering the skin temperature. The measurement results are shown in Table 4 below.

TABLE 4

| | Descriptions | Change in the skin temperature |
|---|---|---|
| Example 5 | Reference Example 1 impregnated into expanded urethane foam and then applied to the skin using NBR puff | −3° C. |
| Example 6 | Reference Example 3 impregnated into expanded urethane foam and then applied to the skin using NBR puff | −4° C. |
| Comparative Example 6 | Reference Example 1 placed in the tube container and then applied to the skin by hand | 0° C. |
| Comparative Example 7 | Reference Example 1 placed in the pump container and then applied to the skin by hand | 0° C. |
| Comparative Example 8 | Reference Example 3 placed in the tube container and then applied to the skin by hand | −1° C. |
| Comparative Example 9 | Reference Example 3 placed in the pump container and then applied to the skin by hand | −1° C. |

As can be seen in Table 4, in the case of Comparative Examples 6 to 9 in which the W/O or O/W emulsion make-up cosmetic composition of low viscosity according to the present invention was placed in the tube or pump container and then applied to the skin by hand, there was little or no change in the skin temperature, suggesting that the composition did not have the effect of cooling the skin. However, in the case of Examples 5 and 6 in which the W/O or O/W emulsion make-up cosmetic composition of low viscosity according to the present invention was impregnated into expanded urethane foam and then applied to the skin using NBR puff, the skin temperature was lowered after applying the composition, suggesting that the composition had the effect of cooling the skin.

TEST EXAMPLE 3

EXAMINATION of PREFERENCE aCCORDING to HARDNESS of EXPANDED URETHANE FOAM

After impregnating the composition of each of Reference Examples 1 and 2 into expanded urethane foam, it was applied to the skin using the cosmetic applicator NBR puff. During the application of the composition, the difference in preference between the hardness values of the expanded urethane foam was examined. In the preference test, 50 women participants were divided into two groups: a group using the composition of Reference Example 1, and a group using the composition of Reference Example 2, each group consisting of 25 persons. The participants were required to apply the compositions to the skin for 2 days, and then to select one having excellent usability from among the compositions. In Examples 7 to 9, the composition of Reference Example 1 was impregnated into urethane foam, and in Examples 10 to 12, the composition of Reference Example 2 was impregnated into urethane foam. The test results are shown in Tables 5 and 6 below.

TABLE 5

| | Kind of impregnated contents | Hardness of the expanded urethane foam after impregnation(ASKER hardness F type) | Preference(%) |
|---|---|---|---|
| Example 7 | Reference Example 1 | 5 | 5 |
| Example 8 | Reference Example 1 | 80 | 10 |
| Example 9 | Reference Example 1 | 40 | 85 |

TABLE 6

| | Kind of impregnated contents | Hardness of the expanded urethane foam after impregnation(ASKER hardness F type) | Preference(%) |
|---|---|---|---|
| Example 10 | Reference Example 2 | 5 | 5 |
| Example 11 | Reference Example 2 | 80 | 5 |
| Example 12 | Reference Example 2 | 40 | 90 |

As can be seen in Tables 5 and 6 above, in all the cases in which the compositions of Reference Examples 1 and 2 were used, the case in which the hardness of urethane foam after imprenation of the compositions was 40 showed the highest preference.

TEST EXAMPLE 4

EXAMINATION of PREFERENCE ACCORDING to TYPE of CONTAINER

The composition of each of Reference Examples 1 and 2 was placed in expanded urethane foam having a hardness of 40 as measured after impregnation with an ASKER hardness tester (type F), and then was placed in a pack container (Examples 13 and 14) and in a tube container or pump container (Comparative Examples 10 to 13). The difference in preference between the compositions contained in the containers was examined. In the preference test, 50 women participants were divided into two groups: a group using the composition of Reference Example 1, and a group using the composition of Reference Example 2, each group consisting of 25 persons. The participants were required to apply the compositions to the skin for 2 days, and then to select one having excellent usability from among the compositions. The test results are shown in Tables 7 and 8 below.

TABLE 7

| | Descriptions | Preference (%) |
|---|---|---|
| Example 13 | Reference Example 1 impregnated into the urethane foam and then packaged in the pack container | 80 |
| Comparative Example 10 | Reference Example 1 packaged in the tube container | 10 |
| Comparative Example 11 | Reference Example 1 packaged in the pump container | 10 |

TABLE 8

| | Descriptions | Preference (%) |
|---|---|---|
| Example 14 | Reference Example 2 impregnated into the urethane foam and then packaged in the pack container | 90 |
| Comparative Example 12 | Reference Example 2 packaged in the tube container | 5 |
| Comparative Example 13 | Reference Example 2 packaged in the pump container | 5 |

As can be seen in Tables 7 and 8 above, in all the cases in which the compositions of Reference Examples 1 and 2 were used, the case in which the compositions impregnated into the urethane foam were packaged in the pack container showed a significantly high preference compared to the case in which the compositions were packaged in the tube container or pump container.

TEST EXAMPLE 5

ADDITIONAL TEST for FORMULATION STABILITY—BASED on HARDNESS of URETHANE FOAM To evaluate the formulation stability of the urethane foam based on hardness, the cosmetic (viscosity 10,000 cps) of Reference Example 1 was impregnated into each of urethane foams (10mm thick) having a hardness of 5, 10, 15, 25, 35, 45, 55, 65, 70, or 80 after impregnation and measured in regard to stability. The measurement results are presented in Table 9.

TABLE 9

| Div. | After 10 days at 45° C. | After 5 days of 8-hour cycle [45° C. →30° C.→freeze (−10° C.)] | After 2 days at 50° C. |
|---|---|---|---|
| Hardness 5 | Separation | Separation | Separation |
| Hardness 10 | A little separation | A little separation | A little separation |
| Hardness 15 | A little separation | A little separation | A little separation |
| Hardness 25 | A little separation | A little separation | A little separation |
| Hardness 35 | Stable | Stable | Stable |
| Hardness 45 | Stable | Stable | Stable |
| Hardness 55 | Stable | Stable | Stable |
| Hardness 65 | Stable | Stable | Stable |
| Hardness 70 | Stable | Stable | Stable |
| Hardness 80 | Stable | Stable | Stable |

As can be seen from Table 9, the urethane foam with a low hardness of below 35 showed separation of formulation and became unstable over the time and the change of temperature, while the expanded urethane foam of the present invention having a hardness of 35 to 66 as impregnated with a low-viscosity cosmetic was stabilized in formulation over the time and the change of temperature. If not showing any separation of formulation, the urethane foam with hardness above 55 was not effective in providing packability and dispensability for the cosmetics, as can be seen in the following test example 6.

TEST EXAMPLE 6

TEST for PACKABILITY and DISPENSABILITY BASED on HARDNESS of EXPANDED URETHANE FOAM To evaluate the effects of the expanded urethane foam having a specific range of hardness according to the present invention, the expanded urethane foam used as a support for low-viscosity cosmetics was tested in regard to packability and dispensability based on hardness as follows.

<Test for Packability of Expanded Urethane Foam According to Hardness>

The time (sec) required to impregnate 15 g of the make-up cosmetic composition (viscosity: 10,000cps) of Reference Example 1 into an expanded urethane foam (48 mm in diameter and 10 mm thick) was measured according to the hardness of the urethane foam. The 'packability' as used herein was defined as the time (sec) required to pack 15 g of the same cosmetic composition into the expanded urethane foam having a hardness in the range of 5 to 80, that is, 5, 10, 15, 20, 25, 30, 35, 40, 50, 55, 60, 70, or 80 as measured after impregnation with an Asker® durometer type F. The test results are presented in Table 10 and FIG. 3.

Figure 3:
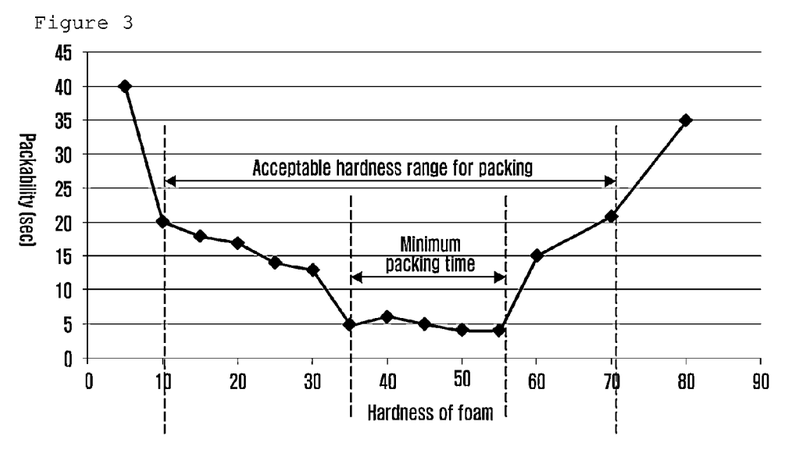
FIG. 3 is a graph showing the results of the test for packability of expanded urethane foam according to hardness.

As can be seen from Table 10 and FIG. 3, the expanded urethane foam with extremely low hardness (i.e., hardness 5) had a poor ability to support the content, thus losing the content downward when packing the content. Accordingly, the packability for 15 g of the cosmetic composition was about 8 times as long as the packability of 5 sec at the optimum hardness.

On the other hand, the expanded urethane foam with extremely high hardness (i.e., hardness 80) had the packability taking such a long time, about 7 times as long as the packability of 5 sec at the optimum hardness.

Accordingly, the hardness for the actually acceptable packability was in the range of 10 to 70, and the maximum packability of less than 5 sec was acquired when the hardness was 33 to 55.

<Test for Dispensability of Expanded Urethane Foam According to Hardness>

A cosmetic applicator puff was put in contact with the expanded urethane foam (48 mm in diameter and 10 mm thick) impregnated with the make-up cosmetic composition (viscosity: 10,000 cps) of Reference Example 1 under pressure of 412 Pa just once. Then, the amount (g) of the cosmetic composition sticking on the puff was weighed by hardness to measure the hardness-based dispensability of the expanded urethane foam. The 'dispensability' as used herein was defined as the amount (g) of the cosmetic composition dispensed on the puff each time the puff was put in contact with the expanded urethane foam having a hardness in the range of 5 to 80, that is, 5, 10, 15, 20, 25, 30, 35, 40, 50, 55, 60, 70, or 80 as measured after impregnation with an Asker® durometer type F. The test results are presented in Table 10 and FIG. 4.

Figure 4:
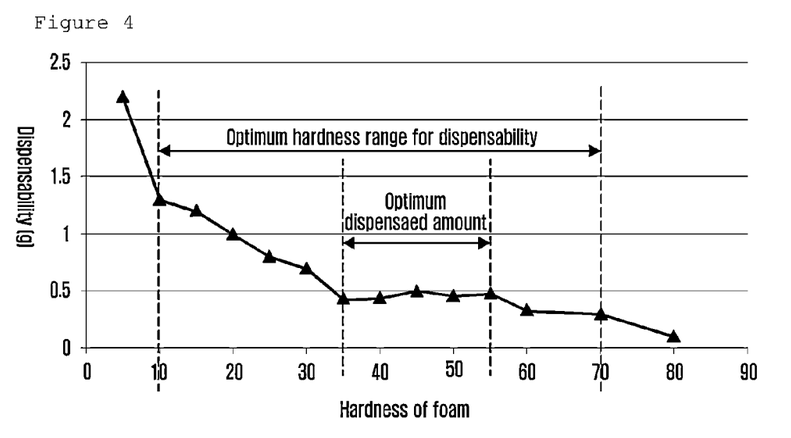
FIG. 4 is a graph showing the results of the test for dispensability of expanded urethane foam according to hardness.

As can be seen from Table 10 and FIG. 4, when the expanded urethane foam had an extremely low hardness (i.e., hardness 5), the dispensed amount of the cosmetic composition per one application was too much as about 2.2 g (5 times the optimum dispensed amount 0.4 g) to apply a uniform make-up on the skin, causing severe contamination of the cosmetic applicator puff to leave unpleasant feelings sanitarily and visually. On the other hand, when the expanded urethane foam had an extremely high hardness (i.e., hardness 80), the dispensed amount of the cosmetic composition per one application was too low as about 0.1 g (one quarter of the optimum dispensed amount 0.4 g), leading to inconvenience in use. It was thus concluded that the dispensed amount per one application was most adequate when the hardness of the expanded urethane foam was 35 to 55.

TABLE 10

| Hardness of support | Packability (sec) | Dispensability (g) |
|---|---|---|
| 5 | 40 | 2.20 |
| 10 | 20 | 1.30 |
| 15 | 18 | 1.20 |
| 20 | 17 | 1.00 |
| 25 | 14 | 0.80 |
| 30 | 13 | 0.70 |
| 35 | 5 | 0.43 |
| 40 | 6 | 0.44 |
| 45 | 5 | 0.50 |
| 50 | 4 | 0.46 |
| 55 | 4 | 0.48 |
| 60 | 15 | 0.33 |
| 70 | 21 | 0.30 |
| 80 | 35 | 0.10 |

TEST EXAMPLE 7

TEST for PACKABILITY and DISPENSABILITY of EXPANDED URETHANE FOAM ACCORDING to VISCOSITY of UV-BLOCKING COSMETIC COMPOSITION To evaluate the excellent effects of the cosmetic composition having a specific viscosity range according to the present invention, the tests were conducted for the packability and dispensability of the expanded urethane foam according to the viscosity of the cosmetic composition.

<Test for Packability of Expanded Urethane Foam According to Viscosity of UV-Blocking Cosmetic Composition>

Figure 5:
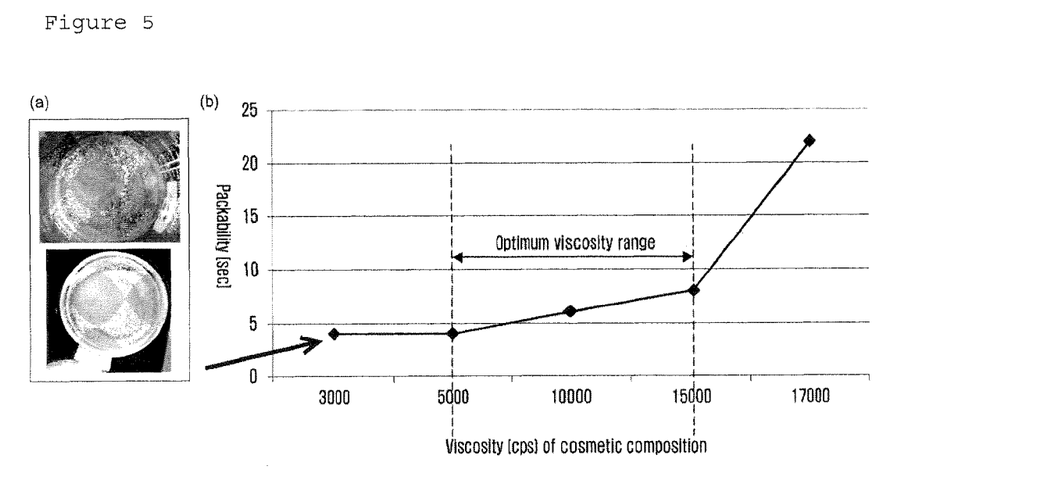
FIG. 5(a) is a set of photographs showing the results of packing the cosmetic composition having viscosity of 3,000 cps into the expanded urethane foam.
FIG. 5(b) is a graph showing the results of the test for packability of expanded urethane foam according to viscosity of UV-blocking cosmetic composition.

The 'packability' as used herein was defined as the time (sec) required to pack 15g of the cosmetic composition having a viscosity of 3,000, 5,000, 10,000, 15,000, or 17,000 cps into the expanded urethane foam (48 mm in diameter and 10 mm thick) having a hardness of 40 as measured after impregnation with an Asker® durometer type F. The test results are presented in Table 11 and FIG. 5.

As can be seen from the results of Table 11 and FIG. 5, the extremely low viscosity (i.e., 3,000 cps) of the cosmetic composition had a short packing time of 4 sec, but with lower emulsification stability, bringing about phase separation of the make-up cosmetic composition and causing the cosmetic composition to flow over the foam without being impregnated into the support (FIG. 5(a)). On the other hand, the extremely high viscosity (i.e., 17,000 cps) of the cosmetic composition led to a long packing time of 22 sec, which was about 3 to 6 times as long as the packability of 4 to 8 sec at optimum hardness.

Accordingly, the cosmetic composition of the present invention which had a viscosity of 5,000 to 15,000 cps acquired optimum packability without incurring phase separation.

<Test for Dispensability of Expanded Urethane Foam According to Viscosity of UV-Blocking Cosmetic Composition>

Figure 6:
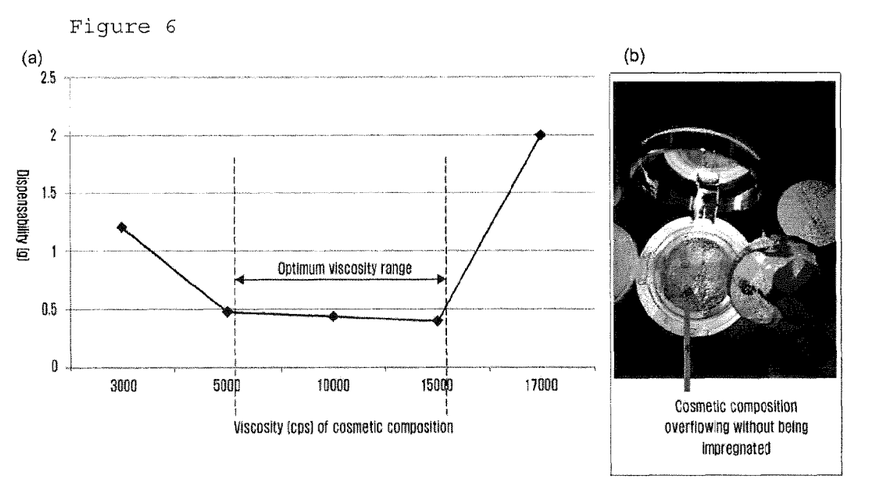
FIG. 6(a) is a graph showing the results of the test for dispensability of expanded urethane foam according to viscosity of UV-blocking cosmetic composition.
FIG. 6(b) is a photograph showing the result of putting a cosmetic applicator puff in contact with the expanded urethane foam impregnated with the cosmetic composition having viscosity of 3,000 cps under pressure of 412 Pa.

A cosmetic applicator puff was put in contact with the expanded urethane foam (48 mm in diameter and 10 mm thick) under pressure of 412Pa. And the amount of the cosmetic composition sticking on the puff was weighed to determine the dispensability of the urethane foam according to the viscosity of the impregnated cosmetic composition. The 'dispensability' as used herein was defined as the amount (g) of the cosmetic composition dispensed on the puff each time the puff was put in contact with the expanded urethane foam (48 mm in diameter and 10 mm thick) and impregnated with 15g of the cosmetic composition having a viscosity of 3,000, 5,000, 10,000, 15,000, or 17,000cps under the same pressure. The hardness of the expanded urethane foam measured after impregnating the cosmetic composition with an Asker® durometer type F was 40. The test results are presented in Table 11 and FIG. 6.

As can be seen from the results of Table 11 and FIG. 6, when the viscosity was low (i.e., 3,000 cps), the amount of the cosmetic composition sticking on the cosmetic applicator puff was too much as 1.20 g (about 3 times the optimum amount of 0.40 g) to apply a uniform make-up on the skin, causing severe contamination of the puff to leave unpleasant feelings sanitarily and visually. When the viscosity was high (i.e., 17,000 cps), the cosmetic composition was not impregnated into the support but flowed over the surface of the expanded urethane foam, increasing the dispended amount to 2.00 g (about 5 times the optimum amount 0.40 g), consequently forming a cake of the composition without uniform make-up application on the skin and thus causing inconvenience in use (FIG. 6(b)).

Accordingly, the dispensability range per each application was optimum without incurring the above-mentioned problems when the cosmetic composition had a viscosity of 5,000 to 15,000 cps.

TABLE 11

|  | Viscosity | | | | |
|---|---|---|---|---|---|
|  | 3,000 | 5,000 | 10,000 | 15,000 | 17,000 |
| Packability (sec) | 4 | 4 | 6 | 8 | 22 |
| Dispensability (g) | 1.20 | 0.48 | 0.44 | 0.40 | 2.00 |

The invention claimed is:

1. A cosmetic container containing an expanded urethane foam impregnated with a cosmetic composition, and an applicator,
    wherein the expanded urethane foam has a hardness of 35-55 as measured after impregnation with a durometer hardness tester type F, manufactured by ASKER, and the cosmetic composition is a UV-blocking cosmetic composition having a viscosity of 5000-15000 cps and containing, in percent by weight based on the total weight of the composition,
    20-80 wt % of an oil-phase component forming the outer phase of the composition,
    0.01-10 wt % of an emulsifying agent having an HLB from 1 to 17,
    1-35 wt % of a UV-blocking agent,
    0.1-20 wt % of a pigment,
    30-70 wt % of a water phased component.

2. The cosmetic container of claim 1, wherein the UV-blocking cosmetic composition is a water-in-oil (W/O) or oil-in-water (O/W) type.

3. The cosmetic container of claim 1, wherein the UV-blocking agent(s) comprise(s) at least one inorganic or organic UV-blocking agent(s).

4. The cosmetic container of claim 3, wherein the inorganic UV-blocking agent(s) is/are at least one selected from a group consisting of titanium dioxide, zinc oxide and iron oxide.

5. The cosmetic container of claim 3, wherein the organic UV-blocking agent(s) is/are at least one selected from a group consisting of octyl methoxycinnamate, octyl salicylate, octocrylene, butyl methoxydibenzoylmethane, oxybenzone, octyltriazone, menthyl anthranilate, 3,4-methylbenzylidene camphor, isoamyl-P-methoxycinnamate, bis-ethylhexylphenol methoxyphenyl triazine and methylene bis-benzotrizolyl tetramethylbutylphenol.

6. The cosmetic container of claim 1, wherein the pigment(s) is/are at least one selected from the group consisting of PMMA (polymethylmethacrylate), silica, nylon, polyurethane, ultramarine, iron oxide, pearl, synthetic mica, mica, talc, sericite and boron nitrate.

7. The cosmetic container of claim 1, wherein the water-phased component(s) is/are at least one selected from the group consisting of purified water, propylene glycol, 1,3-butylene glycol, glycerin, 1,3-PG (propylene glycol), sorbitol, xylitol, hexylene glycol, pentylene glycol, caprylyl glycol, PEG (polyethylene glycol), and various polysaccharides.

* * * * *